United States Patent [19]

Smith et al.

[11] Patent Number: 4,596,350

[45] Date of Patent: Jun. 24, 1986

[54] SURGICAL STAPLER DRIVE APPARATUS

[75] Inventors: George D. K. Smith, Cincinnati; John W. Peter, Loveland, both of Ohio

[73] Assignee: Senmed, Inc., Cincinnati, Ohio

[21] Appl. No.: 608,794

[22] Filed: May 10, 1984

[51] Int. Cl.⁴ .............................................. A61B 17/00
[52] U.S. Cl. ............................... 227/19; 227/DIG. 1; 227/129
[58] Field of Search ............... 128/134 R; 227/67, 19, 227/DIG. 1, 129

[56] References Cited

U.S. PATENT DOCUMENTS

| | | | |
|---|---|---|---|
| 3,873,016 | 3/1975 | Fishbein | 227/DIG. 1 |
| 3,893,612 | 7/1975 | Bone | 227/67 |
| 4,049,177 | 9/1977 | Bussard | 227/67 |
| 4,109,844 | 8/1978 | Becht | 227/DIG. 1 |
| 4,196,836 | 4/1980 | Becht | 227/19 X |
| 4,204,623 | 5/1980 | Green | 227/19 |
| 4,331,277 | 5/1982 | Green | 227/19 |
| 4,349,028 | 9/1982 | Green | 227/19 X |
| 4,416,407 | 11/1983 | Bone | 227/67 |
| 4,502,622 | 3/1985 | Lee | 227/67 |
| 4,523,695 | 6/1985 | Braun et al. | 227/8 |

FOREIGN PATENT DOCUMENTS

3204522A1 2/1982 Fed. Rep. of Germany .
WO81/02269 8/1981 PCT Int'l Appl. .
WO83/00615 3/1983 PCT Int'l Appl. .

Primary Examiner—Paul A. Bell
Attorney, Agent, or Firm—Wood, Herron & Evans

[57] ABSTRACT

In a surgical stapler having a driver and an anvil for forming a staple in tissue, a four-bar linkage is driven by a drive cam which is at least partially curved. The curved cam provides, with the linkage, an increasing mechanical advantage for reducing forces required to operate the stapler and to form a staple. The drive minimizes the range of forces required to operate the stapler throughout an operating cycle. Cam and linkage relationships are disclosed.

13 Claims, 19 Drawing Figures

SURGICAL STAPLER DRIVE APPARATUS

This invention relates to staplers and more particularly to apparatus for driving a surgical stapler.

This application discloses and claims subject matter which is disclosed, but not claimed, in a related copending application, entitled "SURGICAL STAPLER" filed on even date herewith.

In conventional surgical staplers, a staple is driven onto a stationary anvil, disposed at a staple closing or forming station, by a moving driver or former. By virtue of this movement, staple legs are forced into a closed position in which the staple legs engage and secure skin or tissue together. The staple is then released from the stapler and the former returned for another stroke.

Such conventional surgical staplers typically include a handle and a trigger or lever which can be squeezed to operate the former or driver in a linear path for picking up a staple, moving it to the closing station, and forming it about the anvil.

These known surgical staplers are useful, but are attended by a number of structural and functional disadvantages and characteristics which detract from their ease of use and their ease of manufacture.

By way of example, and without limitation, one of the concerns these prior surgical staplers raise is that of the force required to operate the stapler through all of its operating stages. For purposes of discussion, these operating stages generally include a pick-up stage where a staple is picked off a staple supply, a transport stage during which a staple is moved to a staple forming or closing station, a forming stage in which the staple engages an anvil and is closed, and staple ejection and former retraction stages in which the staple is ejected and the former retracted.

Generally, the former or driver is used to pick off the staple from the supply, transport it, and form it. Thereafter, the driver is returned for another cycle. It has thus been required to exert a force on the former or driver to move it through these stages. This driver force is usually generated by applying a manual force to the aforementioned handle and moving its components to cause driver motion through a mechanical connection.

Since surgical staplers are desirably small in structure, as they must be in order to fit into a surgeon's hands for manipulation, the range of movement of the trigger or squeeze handle is practically limited to a small stroke or arc. All the necessary operating forces thus must be applied through a limited stroke movement, and this presents significant structural and operational difficulties.

For example, applicant has observed that the required former or driver operating forces are usually the highest when the staple is being formed, and the staple material is being bent. On the other hand, driver or former forces are relatively low during staple pick-off and staple transport from the supply to the closing station. Moreover, applicant has observed that the distance traveled by the driver during staple forming can be very small as compared to the longer staple transport stroke from the supply pick off to the forming station.

As a result of these relationships, it is not unusual for a surgical stapler to have an operating trigger or handle which must be squeezed with widely varying forces to move it through a complete cycle. Such forces may vary, for example, between fractions of a pound up to 11 pounds or more.

Large force variations are undesirable for several reasons. The manual application of such high forces has the capacity to reduce the precision and steadiness of the staple implanting procedure. At the very point where the staple is engaged with the skin, where maximum preciseness and delicacy are desirable, the surgeon must squeeze the handle much harder, making the process more difficult and perhaps reducing his steadiness with resulting impreciseness.

The constraints of a hand manipulated surgical stapler thus detract from ease of operation and preciseness.

Accordingly, it has been an objective of this invention to provide an improved drive apparatus for a hand manipulated surgical stapler with minimal force input requirements, and minimal input force variations throughout an operating cycle.

To these ends, a preferred embodiment of the invention comprises, in a surgical stapler, a four-bar drive linkage and a drive cam having a cam drive surface, at least a portion of which is curved.

The four-bar linkage includes a bell crank pivoted to the stapler, a link pivoted to one bell crank arm, a second link pivoted to the stapler, and a drive pin pivoting together the two links. The drive pin is captured in a cam slot carried at the end of a swinging trigger lever. The cam slot has a cam drive surface preferably including a curved portion and a straight portion at an upper end thereof, corresponding to the final portion of the operating cycle.

In use, the four-bar linkage is connected to the driver of a stapler through a gear on the linkage and a rack connected to the driver. The curved trigger cam, combined with the driver linkage, serves to disperse the required stapler operating forces more widely across the trigger lever stroke, tending to reduce the extent of input force variations required over the operational cycle of the stapler, and at the same time reducing the maximum input force required for staple forming.

Specifically, a link of the linkage forms a second link angle with respect to an arbitrary reference line. This angle increases throughout an operating cycle. The cam surface engages the drive pin at varying tangent points as the drive is cycled. An angle between the line normal to the tangent at such a tangent point and a second reference line constitutes a cam or slot angle which also varies throughout an operating cycle.

The parameters of the four bar linkage and effective cam or slot angle are selected such that the link angle, minus the effective cam or slot angle, results in a complementary angle which also varies throughout the operating cycle. Preferably, the complementary angle variation generally leads changes in the trigger force required to operate the stapler during the forming stage of the staple and provides an increasing mechanical advantage during operation of the stapler.

While the second link angle generally increases during the overall operation, the resulting complementary angle first decreases, then increases during the forming stage. This controls the application and direction of forces imparted to the drive pin, thus facilitating initiation of the linkage movement, and then facilitating the reduction of the force variation as the linkage is moved to form the staple.

Accordingly, the invention provides many advantages.

Overall operating input forces are substantially reduced by means of the utilization of the four-bar linkage and specific cam drive. At the same time, the required input forces are dispersed widely across the trigger lever stroke so that the range or extent of force variation is reduced. This permits a surgeon to apply a more even squeeze as the stapler is operated through its cycle.

While each of the features which have been and will be described produce their own independent advantages, the combination of the four-bar linkage together with the specifically curved cam, as described herein, provides a much improved drive for a surgical stapler, easy to use and operate, and resulting in a wide dispersion of operating forces over the entire trigger movement, and reduced maximum input forces which may be otherwise required.

These and other objectives and advantages will become readily apparent from the following written description of a preferred embodiment, and from the drawings in which:

FIG. 3a is a top plan view, taken generally along lines 3a—3a of FIG. 3, but including the components omitted from FIG. 3;

FIG. 3b is a cross-sectional view taken along lines 3b—3b of FIG. 3a;

FIGS. 4 and 4a are similar to FIGS. 3 and 3a, except for showing the invention components in one position of the staple transport stage thereof;

FIGS. 5 and 5a are similar to FIGS. 3 and 3a except for showing the invention components at the beginning of the forming stage of the stapler;

FIGS. 6, 6a and 6b are similar to FIGS. 3, 3a and 3b, except for showing the invention components just beyond the end of the staple forming stage, and in the beginning of the staple ejection stage;

FIGS. 7 and 7b are similar to FIGS. 3 and 3b, except for showing the components of the assembled head in an intermediate portion of the retraction or return stage;

Figure 1:
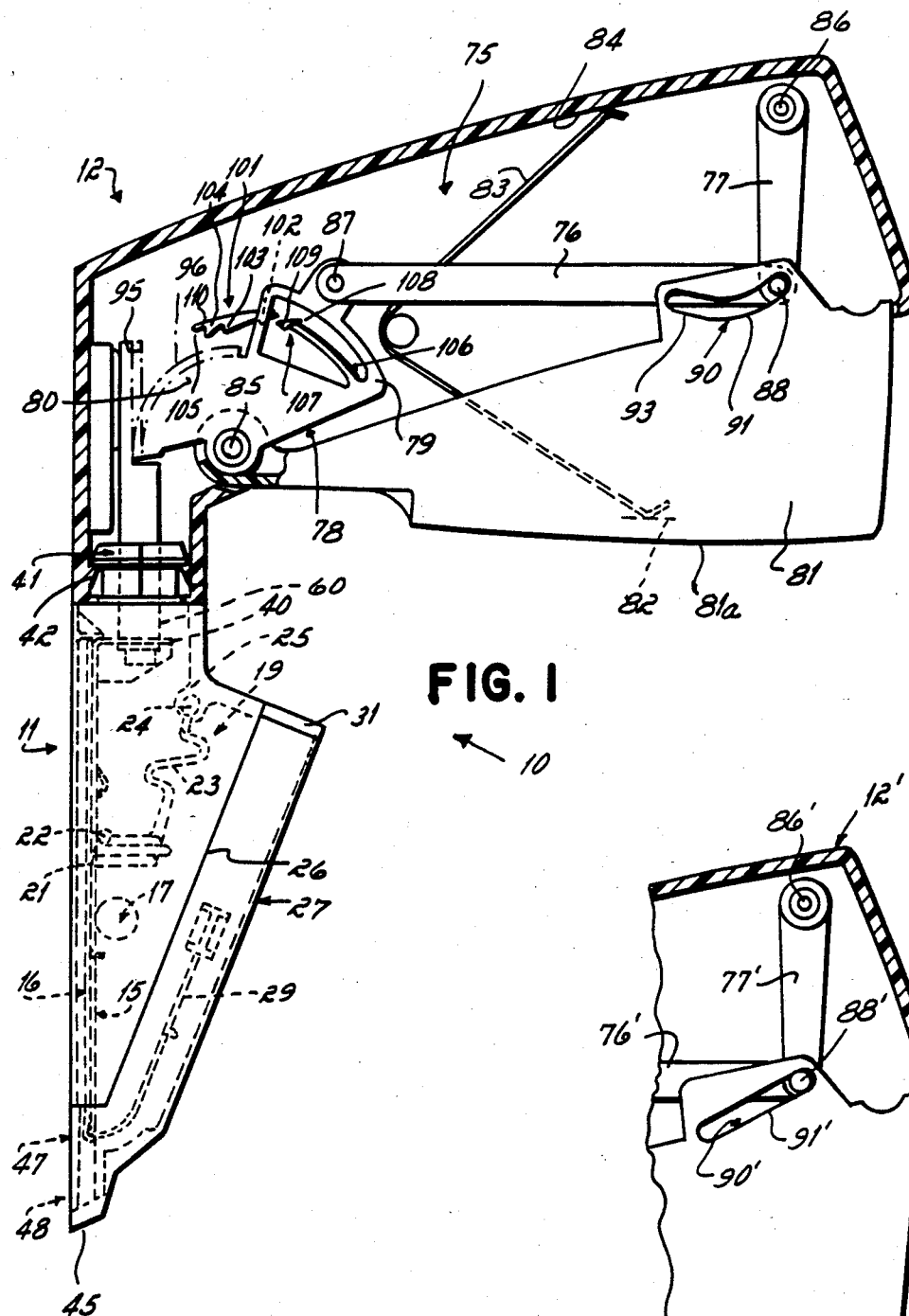
FIG. 1 is a left side elevational view of the surgical stapler invention shown in partial cross-section.
Figure 8:
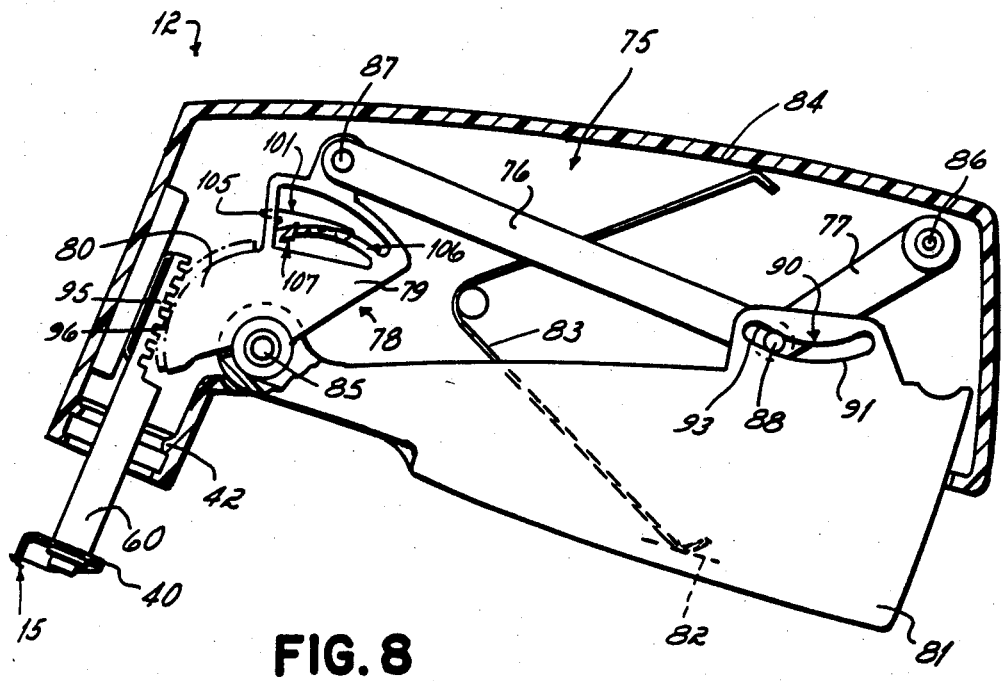
FIG. 8 is a cross-sectional view similar to FIG. 1, showing only the stapler handle section, and showing the operating linkage in an intermediate position.
Figure 9:
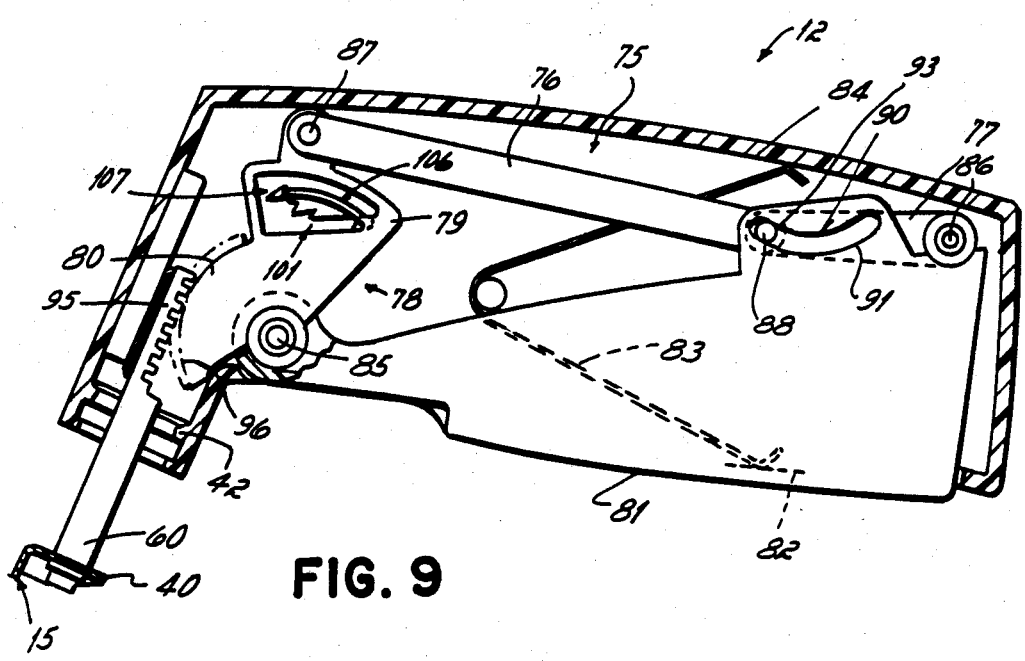
FIG. 9 is a cross-sectional view similar to FIG. 8, but showing the linkage in a fully actuated condition.
Figure 10:
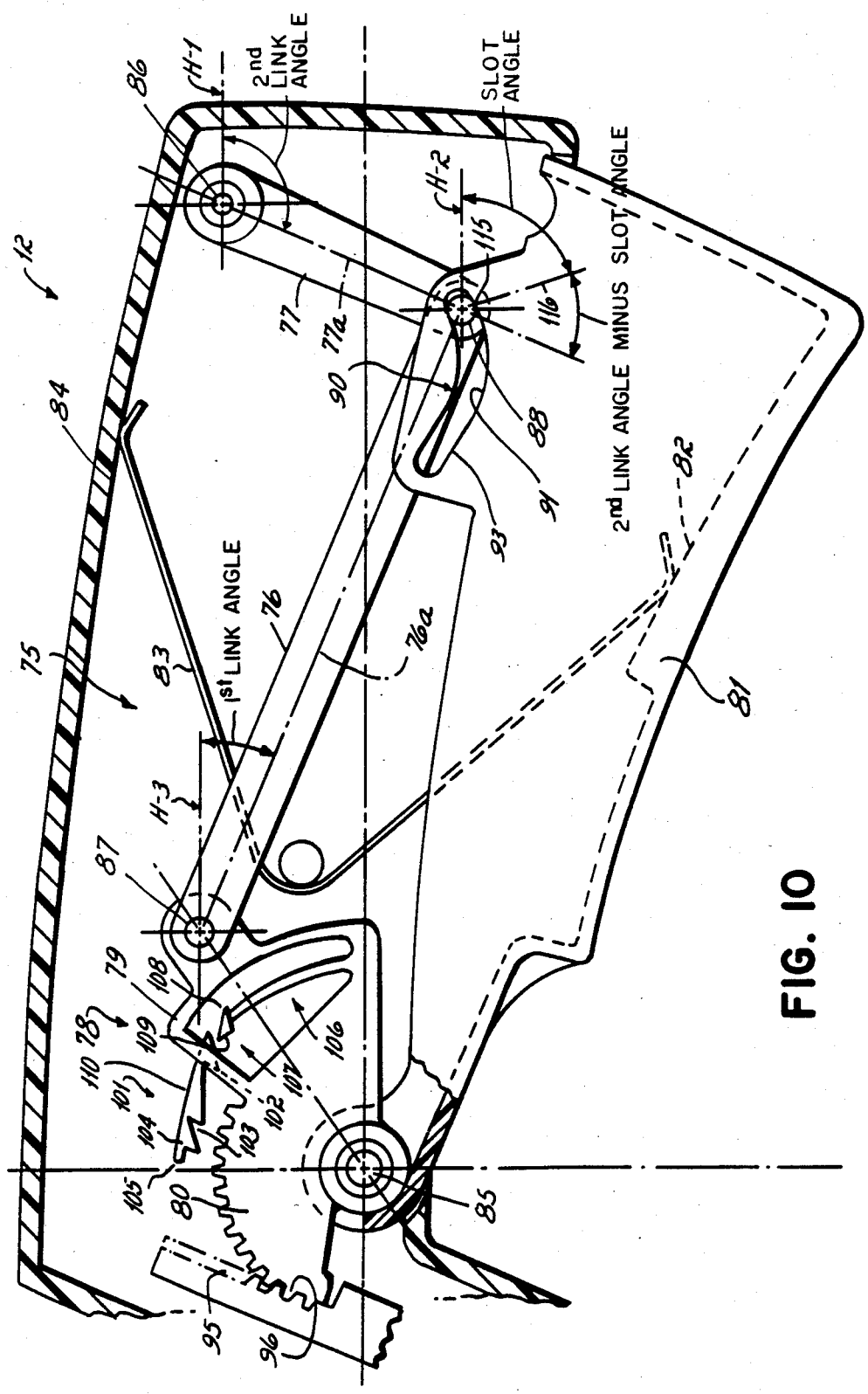
Figure 11:
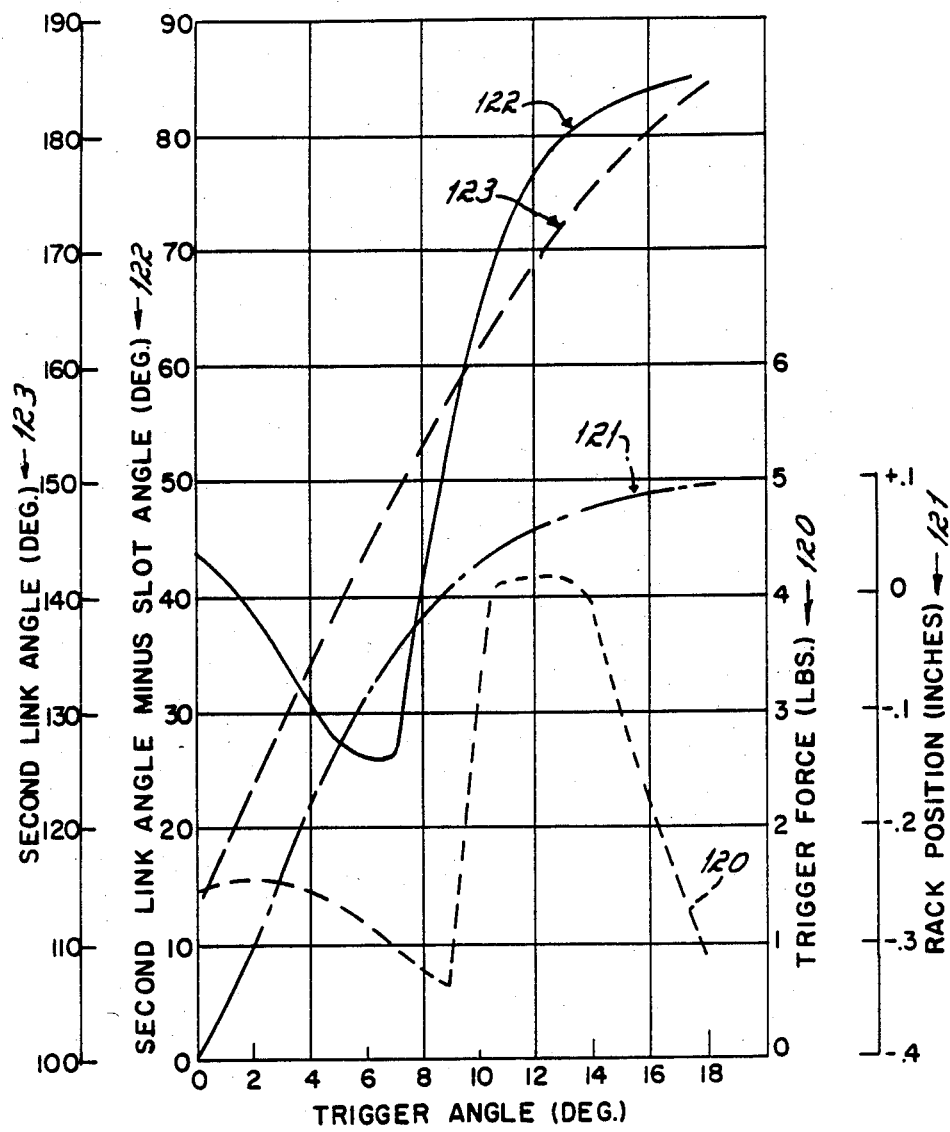

FIG. 10 is an illustrative view similar to FIGS. 1, 8 and 9 and is provided for purposes of description of the relationship of the trigger lever, linkages and operating forces; and, FIG. 11 is a graph showing respective illustrative plots of the result of the second link angle less the cam slot angle for various trigger positions; the trigger angle versus the rack position; the trigger force versus the trigger angle; and the second link angle versus the trigger angle.

Turning now ro tne crawings, it wiii be appreciated that the following description presents alternative and preferred embodiments of a surgical stapler particularly useful for surgical stapling, that is, in the closing of incisions in skin.

A stapler 10, according to the preferred embodiment of the invention, is illustrated in FIG. 1. The stapler 10 includes a head piece or section 11 and a handle piece or section 12. Illustrative views of the head section 11 are shown in FIGS. 2–7, while illustrative views of the handle section 12 and its operation are shown in FIGS. 8–11.

Figure 2:
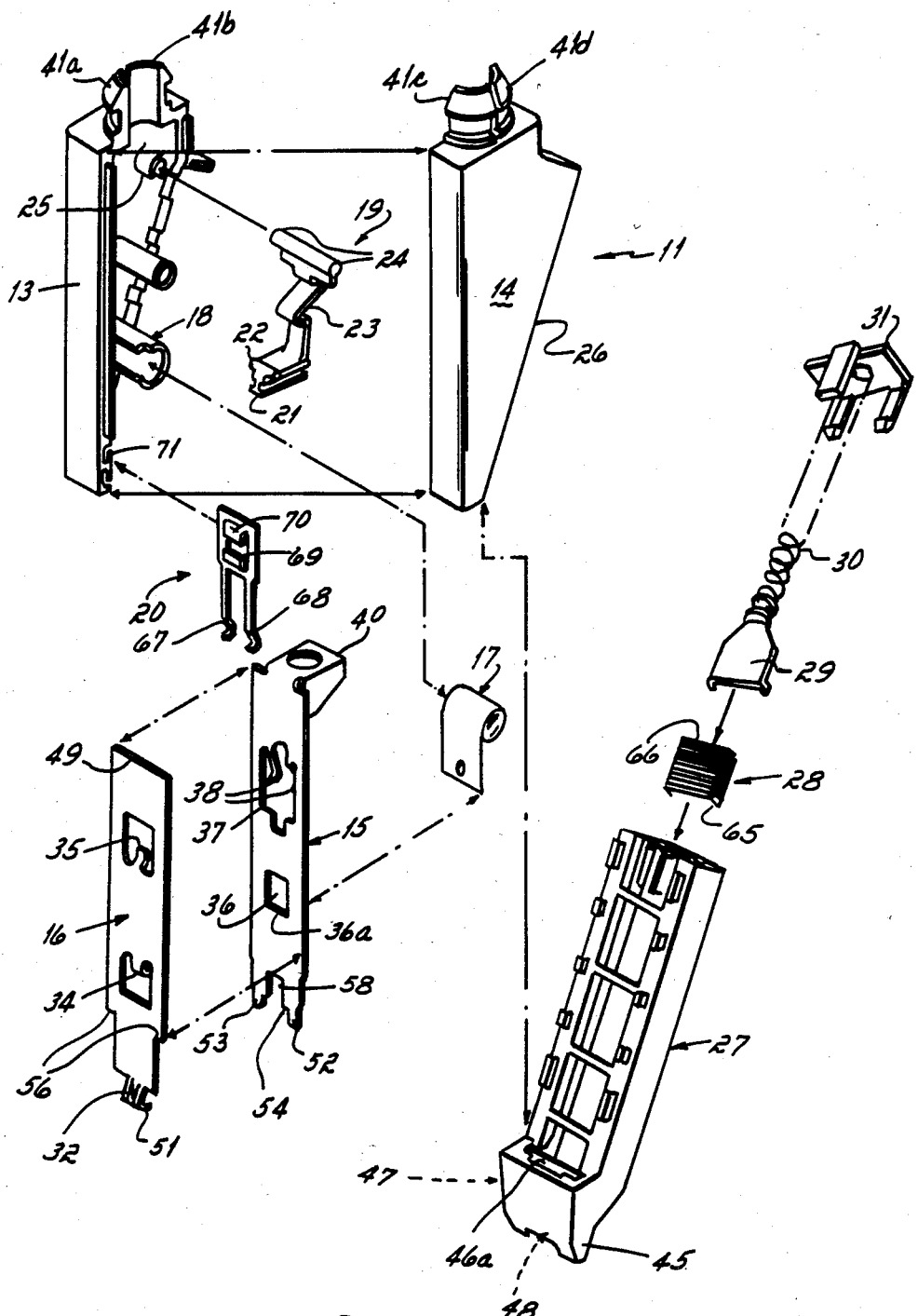
FIG. 2 is an exploded isometric view of various elements of the head of the surgical stapler of FIG. 1.

Considering first the head section 11, its various components are shown in an isometric view in FIG. 2. Head section 11 includes preferably plastic molded female body half 13 and male body half 14 comprising two halves of a head body or housing for containing the other components of the head section 11 as shown in FIG. 2.

Within the head section 11 are located a staple former or driver 15 and an anvil 16. These are slidably disposed, one atop another, in a longitudinal channel 46 formed in the head section 11 by body halves 13, 14.

An anvil return spring 17, of the constant force type, is located within the spring housing 18 of the head section 11, together with an anvil lock 19 and a staple release spring 20. Anvil lock 19 includes an abutment member 21 and a pair of release pins 22. A resilient leaf spring 23 connects the abutment 21 and pins 22 with a rearward mounting boss 24 of the anvil lock 19, which fits within the anvil lock mounting housing 25 of the head section 11.

A staple supply cartridge 27 is mounted along a lower edge 26 of the head section 11, and is configured to contain a predetermined supply of crown formable surgical staples 28. Staples 28 are urged forwardly within cartridge 27 by means of a follower 29, follower spring 30 and keeper clip 31. Keeper clip 31 is preferably a snap-on member, to permit ease of staple loading, and can be used whether or not the stapler is disposable or reloadable.

Figure 3:
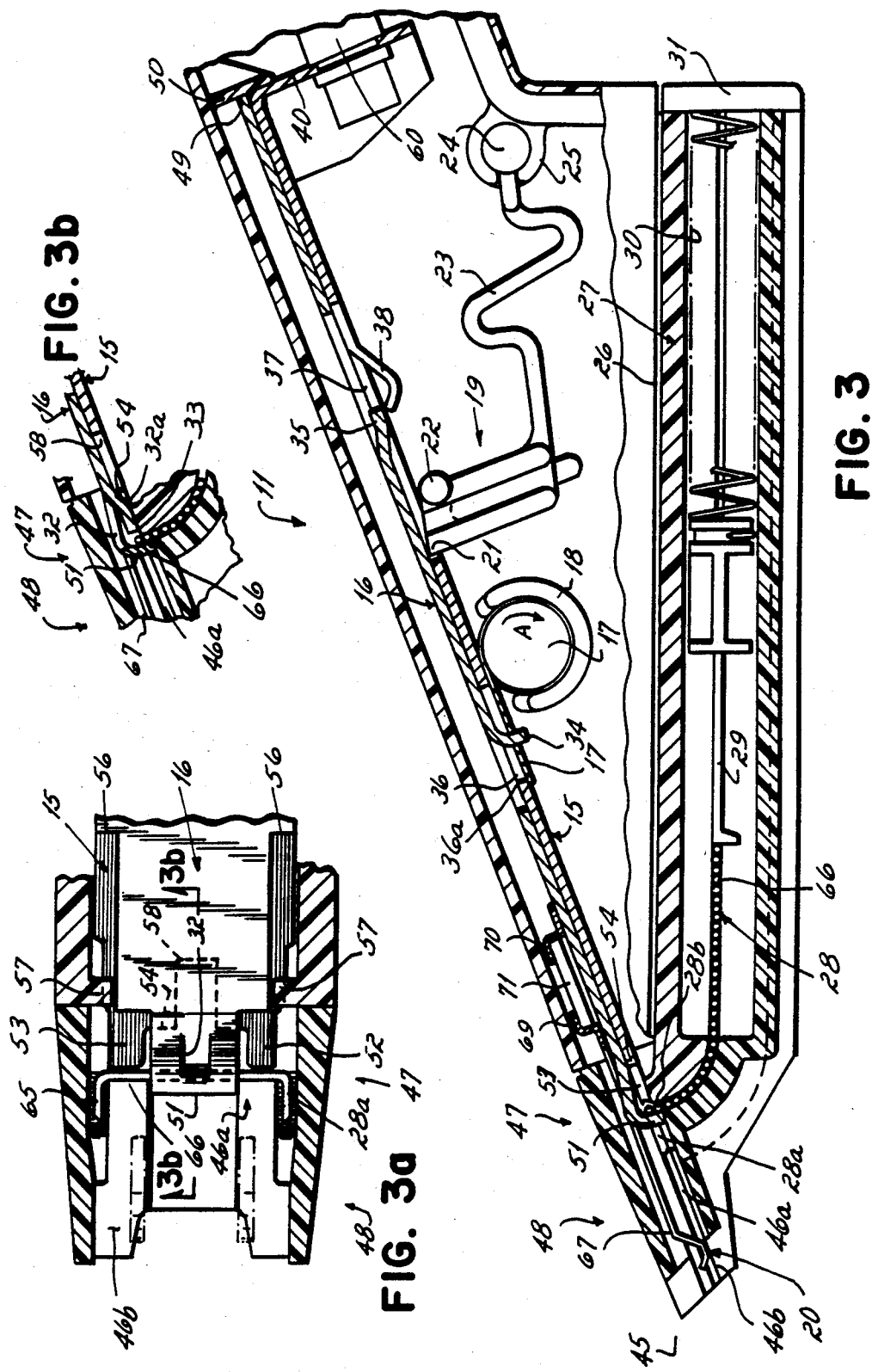
FIG. 3 is a longitudinal cross-sectional view of the assembled head of the invention, in the staple pick-off position, with various components not being shown for clarity, those components being shown in FIG. 3b.

Returning momentarily to the anvil 16 and the driver 15, the anvil 16 is provided with a turned-down spring tab 34 for the purpose of connecting the anvil to the return spring 17, as shown in FIG. 3. The anvil is also provided with a turned-down anvil latching tab 35. The anvil spring tab 34 and the anvil latching tab 35 are directed downwardly from the plane of anvil 16 so as to extend into or through the plane of the former 15, as best shown in FIG. 3. Former 15 includes an aperture 36 for receiving tab 34 of the anvil 16 and also includes an aperture 37 for receiving the anvil latching tab 35. The forward edge 36a of aperture 36 is positioned so as to engage anvil tab 34. This further facilitates rearward anvil motion, once anvil lock 19 has been released, by exerting the force of the retracting driver on the anvil as well during at least part of the rearward anvil motion.

Driver 15 is provided with anvil lock release member 38 depending downwardly therefrom. Driver 15 also includes a connecting tab 40 which extends downwardly at right angles thereto and at the rearward end thereof. Connecting tab 40 is particularly adapted for connection to a manually operable, spring returnable driving apparatus, as will be hereinafter described.

Head section 11, as perhaps best seen in FIGS. 1 and 2, also has a rearwardly extending and rotatable coupling member 41 which can be snapped into the handle 12 and beyond the detents 42 therein in order to permit the head piece 11 to be rotated in at least one plane with respect to the handle 12. Rotatable coupling 41 comprises four coupling quadrants 41a, 41b, 41c and 41d, which provide the resilience necessary for the snap-in coupling of the head section 11 to the handle 12.

Further, and with reference to FIGS. 1 and 3, it will be appreciated that the head section 11 defines several various stations therein. For example, the staples 28 are supplied through the cartridge 27 into a relatively flat thin profiled forward end 45 thereof mounted forwardly of the body halves 13, 14. The staples 28 are supplied to a staple channel 46a at a staple pick-up station 47. Staple channel 46a is within the cartridge 27 and constitutes a continuation of longitudinal channel 46 in head section 11. Staples are sequentially supplied to the pick-up station 47 and are thereafter transported through the channel 46a to a forming or closing station 48. As noted in FIG. 1 and in numerous other figures, it will be appreciated that the forward end 45 of the head section 11 presents a flat, thin-profiled cross-section as compared with the remainder of the head section 11 and cartridge 27. This construction facilitates visibility of the staple and the tissue area to be stapled during utilization of the stapler 10.

Turning now to FIGS. 3–7, further structural and operational details of the head section 11 of the stapler 10 will be described. These figures illustrate the structure and the operation of the various components of the head section 11 from their normal at-rest position proximate the pick-up station 47 through transport, forming, ejection and partial retraction stages, as will be described.

For descriptive purposes, it will be appreciated that the stapler is operable to pick off a single staple from the supply of staples 28, transport it through a staple channel 46a to a forming station 48, close the staple at the forming station 48 and into adjacent tissue, and thereafter eject the staple and retract the operative components of the stapler 10 for another stapling cycle.

Also, for purposes of description, it will be appreciated that the anvil 16 includes, at its forward end, an anvil means comprising an abutment or forming surface 51 which extends transversely to the staple channel 46a at the pick-up station 47.

Anvil 16 also includes an integral staple keeper 32 stamped out of the anvil in the area of the abutment surface 51. Keeper 32 includes a forward end 33 defining a pocket for receiving the crown of a staple between end 33 of keeper 32 and the abutment surface 51. Keeper 32 also includes a staple control surface 32a as will be explained.

Moreover, it will be appreciated that the driver 15 includes forward projections 52 and 53 for engaging the crowns of the unformed staples, and a central forward section 54 extending transversely between the projections 52 and 53. Central section 54 spaces the projections 52 and 53 a distance apart which is preferably slightly greater than the width of the anvil abutment 51. As noted in FIG. 3, the anvil abutment 51 extends transversely to staple channel 46a as well as transversely and through the plane of the driver 15.

A cut-out 58 is disposed in central section 54. Forward projections 52 and 53 of driver 15 are relieved, as shown in FIG. 2, so that their outer edges are spaced inwardly of the elongated outer edges of the driver 15. The combination of the cut-out 58, together with the relieved areas on the outer sides of projections 52 and 53, render the projections more flexible, in a transverse direction, than they would be if simply protruding straight forwardly of driver 15 and without cut-out 58.

Such flexibility facilitates staple forming and closing, the legs slightly spreading apart as the staple is initially formed and then moving inwardly to finally close the staple once it has been formed about the anvil.

FIG. 3 depicts the stapler head section 11 in an at-rest, fully retracted stage, at which time the driver 15 and the anvil 16 are fully retracted.

From FIG. 3, it will be appreciated that while the anvil 51 is located at the staple pick-up station 47, the forward projections 52 and 53 of the driver 15 are slightly further withdrawn in a rearward direction to provide a clearance of about 0.010″ in order to permit a staple 28a to be received between the forward projections or ends 52 and 53 of the driver 15 and the anvil abutment 51.

In this position, it will be appreciated that the spring 17 is biased in a direction indicated by arrow "A" so as to urge the anvil 16 in a rearward direction. Surface 49 is engaged by a rearward stop 50 comprising an integrally molded abutment in the body halves 13, 14. This stop 50 also restrains any further rearward movement of driver 15. Also, forward edge 36a of the aperture 36 in driver 16 (FIG. 2) has engaged tab 34 of anvil 16 so as to limit the longitudinal separation of the anvil abutment surface 51 from the forward portions of driver 15. In this position then, the driver 15 and anvil 16 are thus disposed in their rearwardmost position.

Continuing now with the operation of the stapler, driver 15 is rotatably connected to the operating handle 12 by means of the forward end of a drive pin or rack member 60, as will be described. Member 60 may be bifurcated and is rotatably coupled to the tab 40, extending from driver 15. Member 60 is preferably snapped into tab 40 when head piece 11 and handle 12 are rotatably coupled together. Pin 60 is operable to push the driver 15 forwardly, that is, to the left as viewed in FIG. 3. This forward motion picks off a staple 28a from the supply 28, transports the staple to the forming station 48, and forms and closes the staple at the forming station 48. Thereafter, the driver 15 is retracted or returned for another cycle. As will be further described, the driver 15 moves through a stroke of about 0.395″ from its retracted position through the pick-up station 47 and transport stage to the forming station 48. The forming stroke of driver 15 is about 0.100″, altogether requiring a total driver stroke of about 0.495″.

Returning to FIG. 3a, it will be appreciated that a staple 28a, comprising legs 65 and a crown 66, is about to be engaged or clamped between the anvil abutment 51 and the driver projection 52 and 53 the staple being held therebetween once the driver 15 is urged slightly forwardly to engage and pick the staple off at the pick-up station 47. In this position, it will be appreciated that the staple 28a is disposed in the staple channel 46a with the staple legs 65 pointing forwardly.

It will also be appreciated that when the driver 15 clears the staple pick-off station 47, and the anvil 16 is in its rearwardmost position, a staple is ejected from the supply line of staples 28 into the staple channel 46a, and is captured in the pocket defined between the anvil abutment surface 51 and the forward end 33 of the staple keeper 32. The staple cannot fall further into the channel 46a nor can any other staple enter the channel. As the driver 15 and anvil 16 are moved forwardly, the lower surface 32a of the keeper 32 provides an abutment preventing staple 28b from entering channel 46a (FIG. 3b). Components of the driver 15 immediately follow the anvil so that each staple is continuously and positively controlled, and there is no opportunity for inadvertent or undesirable injection of two staples into channel 46a such as would jam the stapler. Even if driver 15 were released prior to the time the anti-backup ratchet (to be described) was engaged, the returning staple keeper 32 would prevent injection of a second staple 28b into channel 46a.

It will also be appreciated that the spring 23 of the anvil lock 19 urges the latch abutment 21 upwardly and into the aperture 37 of the driver 15 where the abutment 21 strikes the underneath side of the anvil 16, but ineffective to block forward motion of the anvil 16 or the driver 15.

Figure 4:
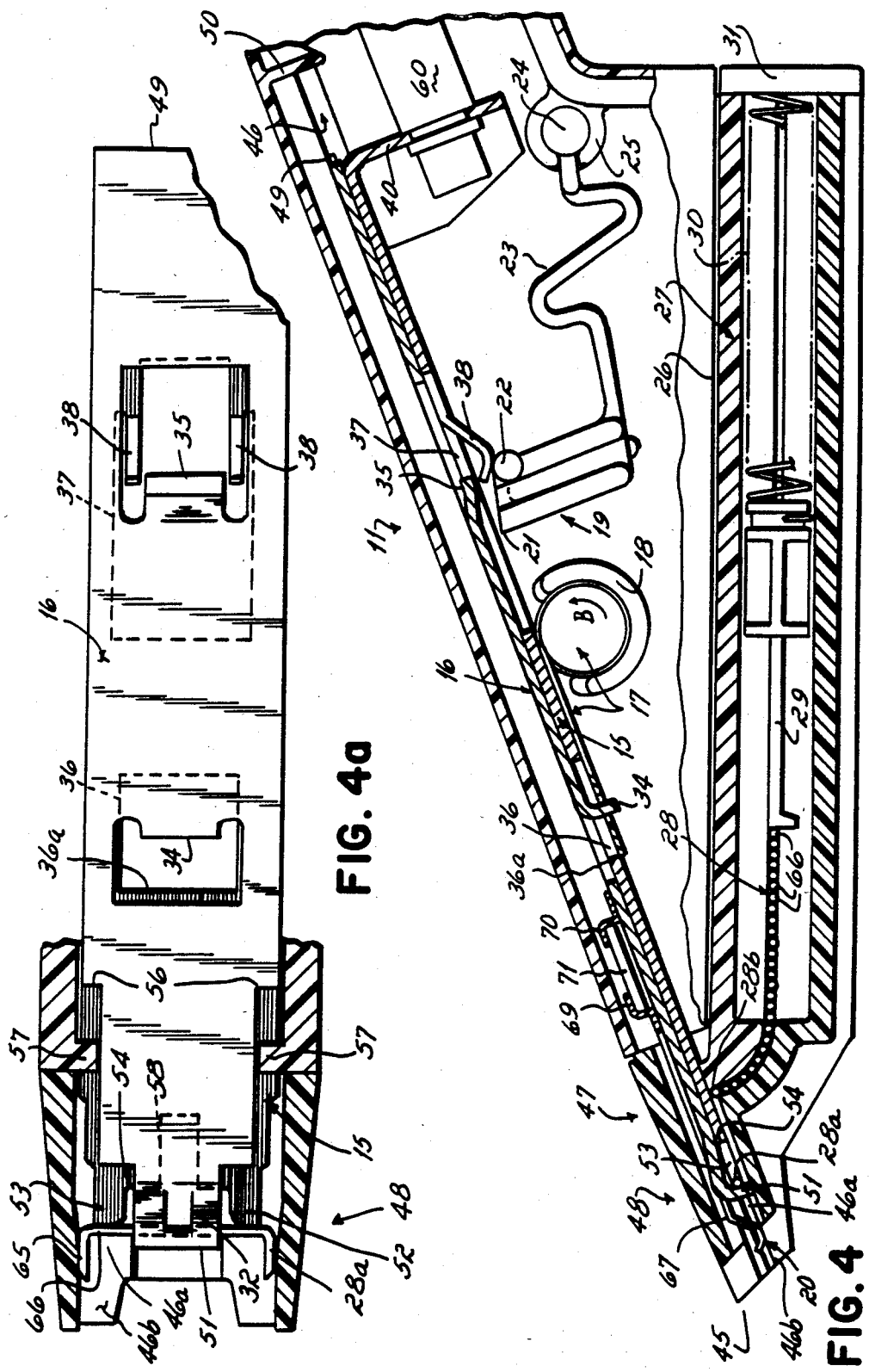

Turning now to FIG. 4, it will be appreciated that the driver 15 and the anvil 16 have been moved forwardly by virtue of the forward driving motion of the connecting pin or rack 60, moving the staple from the pick-up station 47 through a transport stage and toward the forming station 48. During this transport stage the projections 52 and 53 have engaged the staple crown 66 and pushed it forwardly against the anvil abutment 51, carrying both the staple 28a and the anvil 16 forwardly in the direction of movement of the driver 15. The legs 65 of the staple 28a are directed in a forwardly direction during the transport stage. It will also be appreciated that the driver 15 has moved past the pick-up station 47 so that a subsequent staple 28b is maintained in the supply channel of the cartridge 27, and is not permitted into the staple channel 46a.

It will also be appreciated that the constant force spring 17 has been uncoiled in the direction of arrow "B" by virtue of the driver 15 pushing the staple 28a and the anvil 16 forwardly against the bias of the spring 17. This spring bias normally urges the anvil 16 rearwardly. As a result of this construction, the staple 28a, is held by its crown 66 between the anvil 51 and the driver projections 52 and 53, thus positively controlling the staple 28a in its position within the channel 46a. Staple keeper 32 also acts as a positive staple control element, maintaining the staple 28a in proper position, even if the driver is slightly released. The staple is not only positively held in its correct position, but is prevented from falling forwardly and out of the head section 11.

It will also be noted in FIG. 4 that the anvil lock release members or springs 38 of the driver 15 have moved forwardly over the pins 22 and urged the anvil lock 19 downwardly, as viewed in FIG. 4, against the spring bias of the leaf spring 23 thereof. In this regard, it will be noted that the anvil lock release members 38 are travelling forwardly and will eventually pass the pins 22, permitting the anvil lock 19 to again move upwardly.

It will also be noted that throughout the transport stage, the staple 28a is preferably retained in its unformed condition.

FIG. 5a illustrates the operation of the stapler at the closing or forming station 48 in the initial forming of the staple 28a. When anvil 16 reaches this position, anvil stop surfaces 56 engage respective stops 57 on either side of anvil 16 to prevent its further forward motion. These stops 57 are located near the forward end of longitudinal channel 46 in which anvil 16 slides, and comprise molding abutments in body halves 13, 14 on each side of the anvil 16. These stops 57 lie in the plane of the anvil 16 and do not interfere with continued forward motion of driver 15.

At forming station 48, the anvil 16 is held in a stationary position, while the projections 52 and 53 of the driver 15 continue to move forwardly against the outer portions of the staple crown 66, bending the crown forwardly around the anvil abutment 51. The legs 65 of the staple 28a are shown in FIG. 5a, bent inwardly so that their tips are moved toward each other and toward the final closed position which is shown in FIG. 6a.

Figure 5:
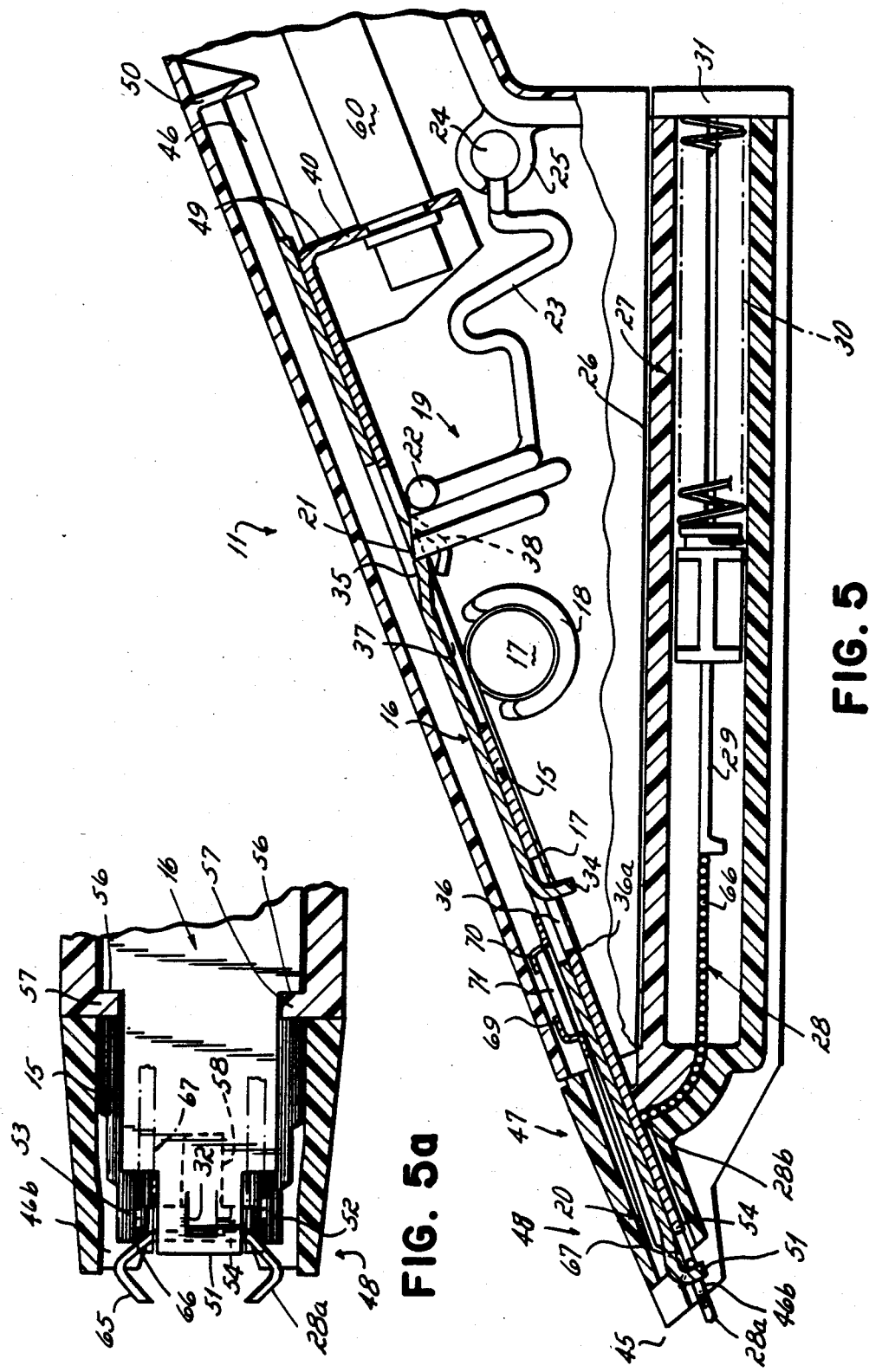

In FIG. 5 it will be appreciated that the staple 28a is held by the anvil abutment 51 at the closing or forming station 48 in a position so that it is directly under the spring legs 67 and 68 of the staple release spring 20. Nevertheless, the staple 28a is not ejected, but is held in the stapler 10 at the forming station 48 by virtue of the fact that it is formed about the anvil abutment 51 by the components of driver 15, and is frictionally held between these two members at this point in time. Also, staple 28a is held by internal surfaces 46b of the channel 46a as best shown in FIG. 5a.

It will also be appreciated that the staple release spring 20 includes mounting tabs 69 and 70 which are shaped to fit about the body half molding 71. This holds the release spring 20 in fixed longitudinal position within the stapler, yet permits the legs 67 and 68 to flex from their normal position as shown in FIG. 4, for example, to a raised position as shown in FIG. 5. This accommodates the entry of the staple 28a into the closing or forming station 48. At this point in time, it will be appreciated that the constant force spring 17 is fully extended and continues to exert a rearward motion on the anvil 16 in order to bias and urge the anvil 16 in a rearward direction.

As shown in FIG. 5, the anvil 16 has reached its forming position and lock abutment surface 21 has been urged upwardly, by means of the spring 23, so as to engage the anvil latching tab 35. The anvil 16 is thus restrained from moving rearwardly. It will also be appreciated that the anvil lock release members 38 have moved forwardly of the pins 22 so that the anvil latch abutment 21 can move upwardly through aperture 37 in the driver 15 so as to engage the downwardly extending latching tab 35 of anvil 16.

Figure 6:
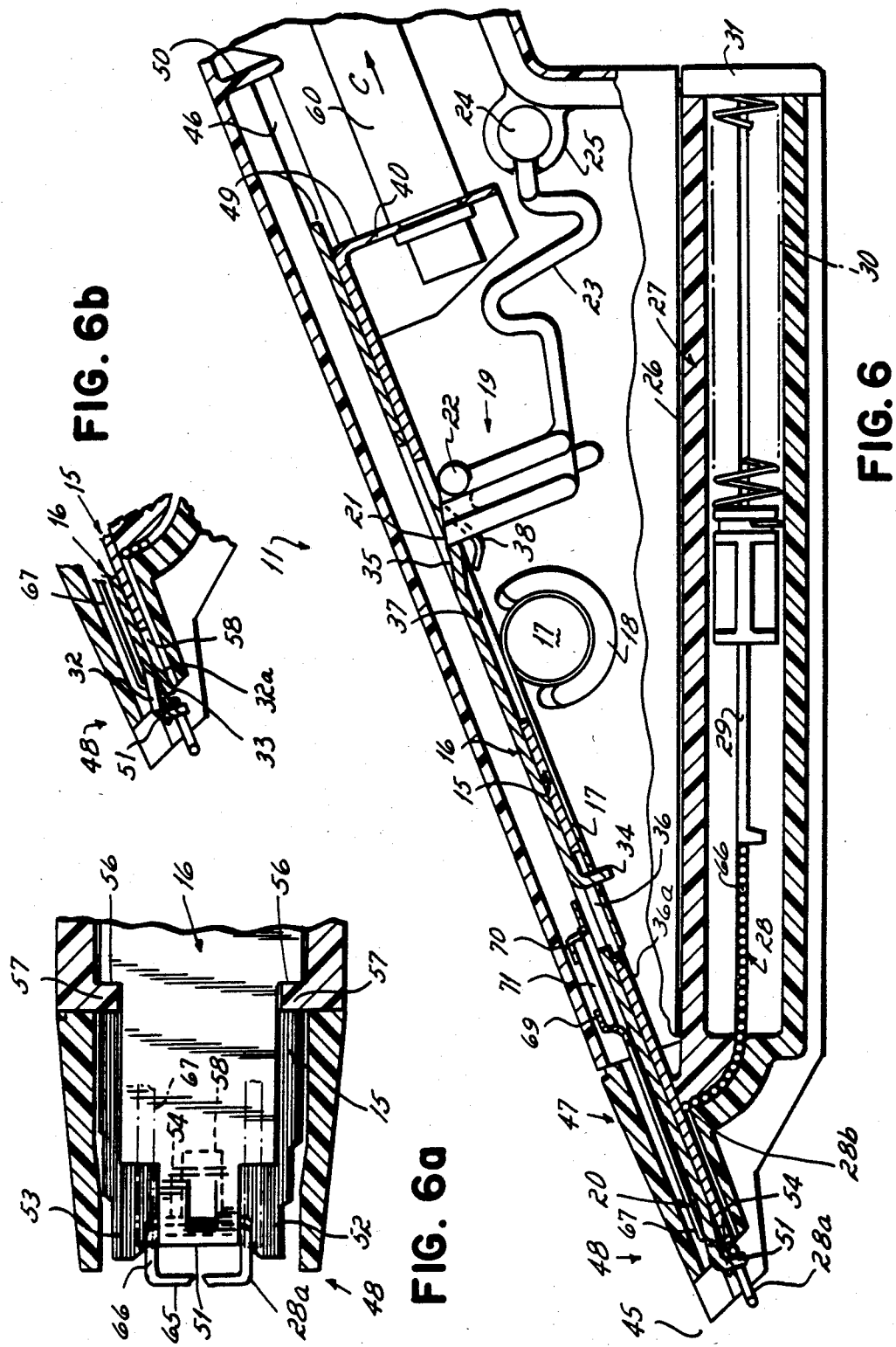

Turning now to FIGS. 6 and 6a, it will be appreciated that the driver 15 has moved forward through its full stroke such that the projections 52 and 53 have engaged the staple crown 66 to deform it and urge the staple 28a into the closed condition (FIG. 6a). As elsewhere described herein, projections 52 and 53 have flexed open upon initial forming, then inwardly to insure a uniform, symmetrically closed staple.

In the closed condition, the staple legs 65 are pointed toward each other with the staple 28a forming an essentially closed figure. Of course, it will be appreciated that the staple legs 65 can be pointed to facilitate the puncture of the skin or tissue by the staples so as to permit the staple 28 to securely hold together the two edges of an incision, for example.

While FIGS. 6 and 6a primarily illustrate the final closed position of the staple 28a, it will also be appreciated from FIG. 6 that the staple can be ejected from the head piece 11 by the spring legs 67, 68 (68 not shown) of the staple release spring 20 only after the driver 15 is retracted rearwardly to clear the staple. This has occurred as a result of withdrawal (see FIG. 7) of the driver surface 54 and legs 52, 53 from the staple 28a by virtue of the exertion of a rearward force in the direction of arrow "C" by the drive pin 60.

Thus, in FIG. 6, the driver 15 is not shown in its fully forward position, but rather in a position where the driver has moved past its fully extended position and has been partially retracted in a rearward direction.

During driver retraction beyond the driver position shown in FIG. 6, enough of the driver 15 clears the staple 28a and staple release spring 20 so that the spring bias of the staple release spring 20 is strong enough to push the staple 28a downwardly from the anvil 51 and thus eject the staple 28a. FIG. 6 thus depicts the staple in its position just prior to ejection as the driver is initially being withdrawn.

At the same time, it will also be appreciated that the lock surface 21 of the anvil lock 19 continues to engage the anvil latching tab 35, retaining the anvil 16 in its fully forward and locked position at the forming station 48, and preventing the retraction of the anvil 16 and the anvil abutment 51 back into the head piece 11. Thus, the anvil 16 is held forwardly until the staple is ejected to prevent retraction of the staple.

Also, the formed staple cannot be retracted, even when urged rearwardly by the exertion of sliding friction thereon by driver 15. Keeper 32 maintains the staple in its forwardmost position.

Figure 7:
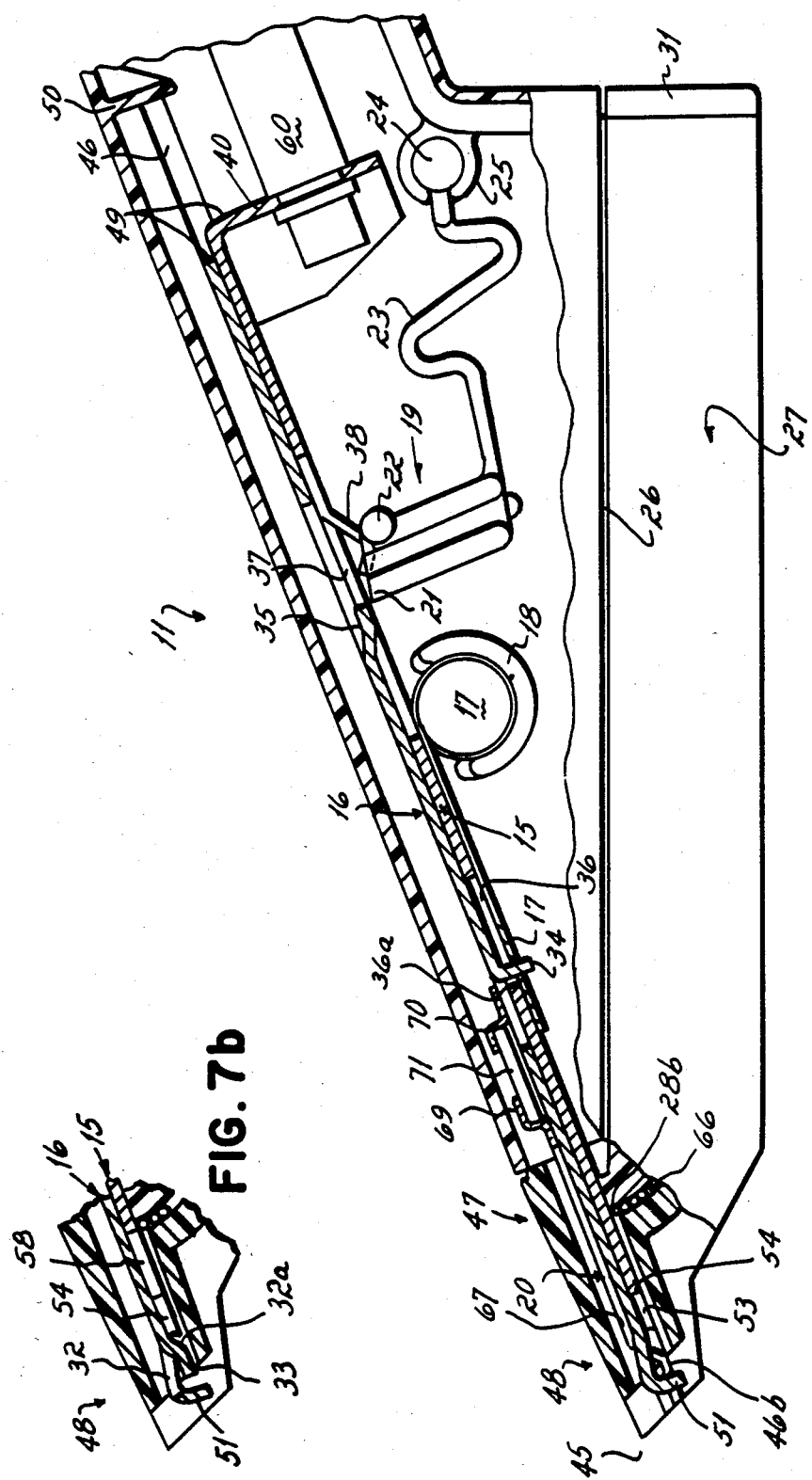

Anvil 16 is held forward by the anvil lock 19 until such time as the spring legs or anvil lock release members 38 are retracted a sufficient rearward distance to engage the pins 22 of the lock 19. This condition is shown in FIG. 7. In FIG. 7, it will be appreciated that the release members 38 have engaged the pins 22 to push the lock with its abutment member 21 downwardly so as to clear the anvil latching tab 35. Also at this position, it will be appreciated that the forward end of the driver 15, including projections 52 and 53, have been retracted substantially rearwardly so as to clear any engagement with any staple adjacent the anvil abutment 51, such that the staple has been rejected.

Accordingly, it should be appreciated that the anvil 15, keeper 32 and abutment 51 are retained in the forming station 48 until such time as the driver 15 has been retracted rearwardly a sufficient distance to both withdraw the anvil lock 19 from the anvil 16, as shown in FIG. 7, and to withdraw the forward ends of the driver 15 from the forming station 48 so as to prevent any binding engagement, by the driver 15, against any staple 28a which might remain at the forming station 48. This ensures that a staple can be positively ejected by the staple release spring 20 and its forward ends 67 and 68 before retraction of the anvil 16. This prevents inadvertent withdrawal of a staple which might be captured between the driver 15 and the anvil 16 and not ejected by the release spring 20. This prevents inadvertent withdrawal of any skin or tissue into the head piece of the stapler upon retraction of the components of the head piece 11.

Once the abutment member 21 is moved downwardly by the members 38, to clear tab 35, the anvil 16 is drawn rearwardly by virtue of the bias of spring 17 retracting into the spring housing 18. This pulls the anvil 16 rearwardly and back toward its position at the pick-up station 47 as shown in FIG. 3. At the same time, the driver 15 is pulled rearwardly by the pin 60, back toward its position at the pick-up station 47 as also shown in FIG. 3. Consequently, as driver 15 and the forward edge 33 of keeper 32 is retracted to pick-off station 47, a second staple 28b is received between the driver 15 and the anvil abutment 51 for use in a subsequent stapling cycle. The spring legs 67 and 68 of the staple release spring 20 remain in their position as shown in FIG. 7, until the new staple 28b is moved forwardly beneath the sprin9 20 at the forming station 48.

As shown in FIG. 7, the anvil lock 19 is released from anvil 16 just prior to engagement of the anvil tab 34 by forward edge 36a of aperture 36 in driver 15. This engagement further urges the anvil rearwardly, and at the same time limits the distance the driver can move rearwardly without positively moving the anvil along with it. In other words, the anvil abutment surface 51, and keeper 32, are always positively maintained within a predetermined maximum distance from the forward components of the driver 15.

As described in part above, and as shown in the figures, there is a relationship between the lateral disposition of the anvil 16 with respect to forward components of driver 15, as limited by engagement of tab 34 with edge 36a in driver 15, and the operative length of surface 32a of keeper 32 in order to insure positive staple control and to prevent jamming. Specifically, and due to the positive engagement of tab 34 by driver 15, the anvil follows the driver rearwardly within a set maximum distance. While the forward forming components of driver 15 are spaced away from the anvil a set distance clearing the channel 46a (see FIG. 3 wherein the rear end of the anvil has engaged a stop, limiting further rearward movement), the length of keeper surface 32a spans the distance preventing injection of any staple into channel 46a until the defined pocket between anvil surface 51 and keeper end 33 are immediately adjacent pick-off station 47. This provides positive staple control, prevents free uncontrolled staples in channel 46a, and at the same time accommodates necessary relative movement of the driver 15 and anvil 16 for positive staple ejection at the downstream forming station during that portion of the cycle.

It will be appreciated that the driver 15 must be driven with various predetermined forces in order to pick up a staple 28, transport it from the pick-up station 47 to the forming station 48, form the staple 28 and thereafter retract to a starting position. Generally, a relatively large driver force is required during the forming stage, that is, from the time when the driver projections 52 and 53 begin to wrap the crown 66 of the staple 28 about the anvil abutment 51, to the point in time where the staple 28 is formed and the driver 15 begins to retract. a relatively smaller driver force is required for moving the driver 15 from the pick-up station 47 through the stage at the forming station 48.

As hereinbefore stated, it is highly desirable to reduce the maximum amount of input force required to move the driver through the forming stage. Yet, at the same time, various constraints limit various driving mechanisms. These constraints are inherent restraints arising from the need to provide a hand-manipulable, surgical stapler which must be easily operated in the hands of a surgeon, for example. Thus, the handle must be relatively small, yet must provide a drive for operating the components of the head piece 11 in the aforesaid manner, and at the same time reduce the variation of input force required to move these components throughout the various stages.

In this regard, it should be appreciated that the total overall preferred driver stroke is about 0.495". At the pick-up station 47, the driver is retracted about 0.010" for staple clearance. Thus, the first portion of the driver stroke is about 0.010" to engage and start a staple on its transport stage. The transport stage itself requires a stroke of about 0.385" and the forming stage requires a stroke of about 0.100", altogether totalling about 0.495".

The various features of the preferred handle section 12 and the various drive components and features thereof for moving the driver 15 and anvil 16 are illustrates in FIGS. 1 and 8–11. FIG. 1 and FIGS. 8 and 9 illustrate initial, intermediate and ending positions of the drive linkage which is depicted therein.

Turning to these figures, it will be appreciated that a preferred embodiment of the stapler includes a handle section 12 which incorporates a four-bar linkage 75.

In this regard, it should also be appreciated that the handle section 12 is preferably manufactured from two handle halves, one of which is shown in FIG. 1 and another similar handle half which is molded in a complementary fashion to constitute the handle section 12 and to provide mounting means for the pivots 85, 86 and various other components.

The four-bar linkage 75 includes a first link 76 and a second link 77 together with a bell crank member 78 comprised of, for descriptive purposes, a first crank arm 79 and a second crank arm 80.

The first and second links 76, 77 and the first and second crank arms 79, 80 comprise the four-bar linkage 75 and the term "four-bar linkage" is used herein to refer to such an overall mechanical linkage in the preferred embodiment hereof.

The handle 12 also includes a trigger lever 81 having a forward surface 81a which can be squeezed to move the trigger lever as will be described. A return spring 83 is disposed between an inner surface 82 of trigger lever 81 and a rear side 84 of handle 12 to constantly urge trigger 81 forwardly. Spring 83 is shown partially in phantom in FIGS. 1, 8 and 9 for clarity.

Considering the further details of the four-bar linkage 75, it will be appreciated that the handle section 12 includes a first pivot 85 and a second pivot 86. These are preferably stationary with respect to each other and are generally disposed within the handle section 12. The pivots 85, 86 may comprise pivot pins. The bell crank 78 and trigger lever 81 are mounted for rotation about the pivot 85 independently of each other. Link 77 is mounted for rotation about the pivot 86.

The four-bar linkage 75 includes two translating or moving pivots or pivot pins 87 and 88. The pivot 87 comprises a pivot pin rotatably connecting an end of the link 76 with the arm 79 of the bell crank 78. The pivot pin 88 comprises a drive pin which connects the lower end of the link 76 with the upper end of the link 77. It will be appreciated that the pivots 87 and 88 are movable with respect to the handle, but operably pivot together the respective links and arms as described above.

Figure 1A:
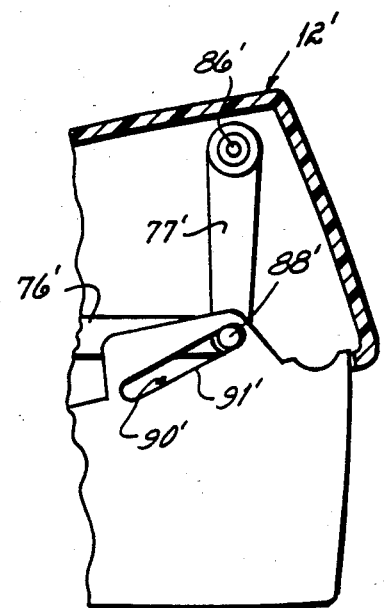
FIG. 1a is a partial view of the stapler of FIG. 1, but showing an alternative cam drive slot.

In order to drive the linkage, a cam slot 90 having a cam drive surface 91 engages the drive pin 88. In an alternative embodiment, as shown in FIG. 1a, the cam slot 90' comprises a straight cam slot having a cam drive surface 91' which is essentially a straight or flat cam surface. In other regards the alternative embodiment is similar to the preferred embodiment.

In the preferred embodiment, however, and as shown in FIGS. 1, 8 and 9, the cam slot 90 is preferably curved but terminates in a straight section 93. Slot 90 has a curved cam drive surface 91 of varying slope with respect to the drive pin 88, as will be hereinafter described.

The drive pin 60 is slidably mounted in the handle section 12 and includes a rack 95 comprising a plurality of rack teeth. The crank arm 80 comprises a toothed gear 96 operably engaging the rack 95 for the purpose of driving the drive pin 60 forwardly in order to operate the components of the head section 11.

While links and crank arms of various lengths can be utilized, in the preferred embodiment the first crank arm 79 is about twice as long as the second crank arm 80, while the link 76 is about two and one-half times as long as the link 77. Moreover, it will also be appreciated that the trigger lever 81 is mounted for movement in an arc of approximately 18° during operation of the stapler. It is also noted that the link 77 moves through an arc of approximately 70° during operation of the stapler. Of course, other lengths of crank arms and links together with varying arcs of movement could be utilized if desirable.

In order to provide the linkage with an anti-backup structure, a rack or ratchet member 101, having forwardly facing ratchet steps 102, 103, 104 and 105 is secured to the handle section 12. A resilient ratchet follower arm 106 is provided with a ratchet head 107 having a ratchet engaging surface 108 and a sliding surface 109.

As shown in FIG. 1, the four-bar linkage is relaxed with trigger 81 not being squeezed in any manner. In this position, the ratchet head 107 is disposed beneath the ratchet 101. However, when the linkage 75 is moved to an intermediate position, the ratchet head 107 engages the ratchet 101 with the ratchet surface 108 engaging the ratchet steps, such as step 103 as shown in FIG. 8, for prevention of a reverse rotation of the bell crank 78. This maintains the stapler components in a forward position and prevents reversal of the drive linkage and the stapler components which could bind or jam the stapler. Once the trigger lever 81 has been squeezed so as to complete a cycle, the ratchet head 107 is disposed above the ratchet 101 and the resiliency of the arm 106 moves the ratchet head 107 upwardly. In this position, the sliding surface 109 is in a position to move upwardly and slide along the rear surface 110 without engaging on any ratchet steps. This permits the full return of the linkage to the unextended position shown in FIG. 1.

Accordingly, the ratchet head 107 engages the steps 102–105 and rides up the ratchet upon operation of the linkage until the linkage is fully extended. The ratchet head 107 then moves over the top ratchet step 105 and can slide along surface 110 to permit return of the linkage to its unextended position. Of course, the ratchet rack 101 could be mounted on the bell crank 78 and the follower or detent 106 mounted on the handle section 12, or on other linkage components, and either of the parts made resilient in order to provide a similar function.

Finally, it will be appreciated that the head 107 moves generally in a stepped-shape arc of one general radius during stapler operation, and in a smooth arc of greater radius upon return of the linkage for another cycle.

FIGS. 10 and 11 are provided in order to further describe the preferred embodiment of the invention and particularly the operation and function of the four-bar linkage 75. In FIG. 10, various reference or axis lines have been added for the purpose of this description. It will be appreciated that the second link 77 has an axis 77a which is disposed at an angle with respect to an arbitrary horizontal axis H-1. This angle is referred to as the second link angle.

Also, it will be appreciated that the cam drive surface 91 of the cam slot 90 engages the drive pin 88 at a tangential point 115. A perpendicular line 116 through this point of tangency also runs through the center of the pivot pin 88 and forms an angle, referred to as the slot angle, with respect to a second horizontal reference axis H-2. Thus, this angle between the axis H-2 and the perpendicular line 116 drawn through the tangential point 115 comprises a slot angle. The angle which is formed between the perpendicular line 116 and the axis 77a of the link 77 forms a complementary angle which is equal to the second link angle less or minus the slot angle.

It will also be appreciated that the link 76 has an axis 76a which forms a first link angle with respect to an arbitrary horizontal reference axis H-3. Moreover, it will be appreciated that the pivot pin 87 moves through a limited arc when the linkage is operated.

Finally, it will be appreciated that the trigger moves about pin 85 through a trigger angle from a position at 0° (FIGS. 1 and 10), to a fully compressed condition (FIG. 9) at about 18°.

In a preferred embodiment of the invention, and while these parameters may vary, it will be appreciated that while the trigger moves through an arc of approximately 18°, the pivot pin 87 will be moved through an arc approximately 47°, while the first link angle will change approximately 14°, increasing or decreasing as the linkage permits. It will also be appreciated that the second link angle moves through about 70°, while the complementary angle, equal to the second link angle minus the slot angle, will change through about 60° as the linkage is operated. These parameters may vary by a few degrees or even more significantly for different size handle sections 12, and for different stapling functions as may be desired.

The curved cam slot 90 optimizes the force delivery characteristics of the four-bar linkage 75 and facilitates the dispersion of the input force required to operate the stapler over the full range of trigger movement. As heretofore stated, it is highly desirable to reduce the range or extent of the force required to operate the stapler. The preferred embodiment of the invention provides a stapler in which the trigger force, i.e., that force which must be applied to the trigger to operate the stapler through its various operating stages, begins at about 1.4 pounds, is reduced to approximately 0.6 pounds, and rises to a maximum about 4.3 pounds near the end of the forming stage. Thereafter, the required trigger force drops off to something less than 1.0 pound. Accordingly, the full range or extent of operating force required in order to operate the stapler is approximately 3.6 pounds between maximum and minimum effort required. Of course it should be appreciated that these force figures, while preferred, are approximations and may vary from stapler to stapler depending on tolerances, friction, materials and the like.

Also, it will be appreciated that the forces exerted by the respective return springs 17 and 83 are selected to insure positive stapler operation without being excessive. In the preferred embodiment, the force of return spring 83 is somewhat larger than the force exerted by return spring 17. Nevertheless, it will also be appreciated that the force exerted by return spring 17 on anvil 16 is supplemented by the force exerted on driver 15 by return spring 83 when anvil tab 34 is engaged by edge 36a of aperture 36 in driver 15.

While in some cases it may be desirable to provide a linkage constructed such that the operating force had substantially no variation, the utilization of the particular handle section 12 and the four-bar linkage 75 as described herein provides a stapler drive with a minimal and extremely useful trigger input force requirement, eliminating undesirable excessive force variations inherent in other known staplers and of much greater magnitude.

In order to illustrate the operation and functional characteristics of the four-bar linkage 76, FIG. 11 illustrates a plot of various parameters throughout the motion of the stapler. In this connection, the curve line 120 illustrates a plot of the amount of trigger input force at the various angular positions of the trigger lever 81. Curve 121 is a plot of the position of the rack or drive pin member 60 versus the trigger angle. In this regard, it will be appreciated that a stroke of approximately 0.495inches has been found to be suitable for the purpose of picking off a staple from the pick-up station 47, transporting it to the forming station 48 and forming the staple for use in closing an incision in skin.

Curve 122 is a plot of the change in the complementary angle for different trigger angle positions. That is, the second link angle less the slot angle as described herein for various positions of the trigger.

Finally, curve 123 is a plot of the second link angle for various positions of the trigger angle as the trigger is moved from 0° to 18°.

For purposes of comparison and illustration, these various plotted functions, 120, 121, 122, and 123, are shown in the same graph with the horizontal axis constituting the trigger angle positions, and the vertical data columns showing appropriate values.

From FIG. 11, several interesting phenomena are observed. For example, it is noted that the forming stage of the staple begins at a trigger angle position of about 9°. That is, the trigger lever is moved through about 9° or one-half its stroke to move the driver from the pick-up station 47 to the beginning of the forming stage, a distance of about 0.395". The remaining 9° of trigger lever motion is used in moving the driver through the forming stage, a distance of about 0.100". At the beginning of the forming stage, the complementary angle represented by curve 122 continues a significant increase, while at the same time the required trigger force rises from its lowest point to a magnitude near its highest value. At the same time, and at the beginning of the cycle represented by the 0° point on the trigger angle line, the complementary angle begins to decrease from about 44° to about 26°, while the required trigger force rises slightly to about 1.5 pounds and then decreases to about 0.6 pounds. Accordingly, it will be appreciated that the change in the complementary angle substantially leads changes in the input trigger forces from the end of the transport stage through the forming stage, and generally leads changes in the trigger force throughout operation with the exception that the complementary angle decreases during initial transport stage movement of the linkage while trigger force slightly rises prior to falling to its lowest value. The complementary angle generally decreases during the initial transport stage movement, helping to overcome initial friction, and increases during the forming stage movement of the linkage.

Also, it will be appreciated that the slope of the plotted curve 121 is generally equivalent to the mechanical advantage of the entire drive linkage and that this slope or mechanical advantage generally increases through the operation of the trigger from its 0 position to its fully compressed position through about the 18° arc mentioned above.

Moreover, it will be noted that as the trigger moves from its 0° position to its 18° position, the second link angle preferably increases from about 114° to about 183° or about 70° overall. Thus, while the second line angle constantly increases, as does the mechanical advantage, the complementary angle (second link angle minus the slot angle) first decreases significantly, then increases.

This relationship facilitates the initial start-up of a stapling operation as opposed to a straight cam slot such as 90' (FIG. 1a) where the actual cam surface would initially be more perpendicular to the direction of cam motion and thus require more start-up force, yet provides the ever increasing mechanical advantage during the staple forming stage to also facilitate reduction of required input forces at the forming stage.

It will be noted that the preferred drive linkage permits use of the first half of trigger movement to produce about 80% of the driver stroke. The entire last half of the trigger movement is used to move the driver through the short remaining 20% of its stroke, including the forming stage.

Several additional comments respecting the physical nature of the respective angles discussed above further illustrate the features of the linkage. It should be noted that as the resultant angle of the second link angle minus the slot angle (curve 122, FIG. 11) becomes smaller, friction greatly increases. If this resultant angle is too small, a friction lock-up condition will occur. Conversely, as the resultant angle increases, the frictional forces experienced decrease.

It should thus also be noted that the high angle values represented by curves 122 and 123 occur at the same general portion of the stroke at which the higher force values (curve 122) occur. In other words, the proportion or ratio of friction forces experienced, to total input force decreases as the staple is formed, and where required operating force is highest. If the values of the angles represented by curves 122 and 123 decreased through the stroke, the amount of required operating forces would increase. Stated in yet another way, the preferred linkage provides a stapler wherein the maximum linkage frictional forces are presented at the beginning of the stroke where less input force is normally required, and linkage frictional forces decrease as the stroke comes to its end during staple forming where higher input forces are normally requires. This effectively facilitates spreading the required input forces over the entire stroke while also facilitating reduction of the maximum force required during the stroke.

The various structures as described, with these relationship disperse required input forces over the entire trigger cycle and, beneficially reduce the maximum variation in input forces over the entire cycle, together with a reduction in the maximum forces required during the forming stage as compared to other known staplers.

Thus, by virtue of these relationships, it is believed that the range or extent of the trigger input force variation from the beginning through the end of the stapling cycle is substantially diminished and improved over other staplers having greater force variations. The curved cam slot 90 is believed to optimize the operation and produce a minimal force variation throughout the cycle.

Accordingly, it will be appreciated that the hand-manipulated surgical stapler described herein provides overall reduced force input requirements and reduced force range variations.

It will be appreciated that the particular structural components of both the head section and the handle section can be modified in size or appearance to perform various surgical fastening tasks, or provide different operating parameters.

It should also be understood that, in use, stapler 10 and the drive apparatus can assume various orientations, and that terms such as "upper," "upward," "down," "downward," "forward," "rearward," "lower" and the like used herein and in the claims are used in association with the accompanying figures solely for the purpose of clarity of description, and are not intended to limit the invention herein.

These and other modifications and advantages will become readily apparent to those of ordinary skill in the art, without departing from the scope of the invention, and applicant intends to be bound only by the claims appended hereto.

We claim:

1. In a surgical stapler having a staple driver, a four-bar linkage for operating the staple driver and comprising:
   a bell crank operatively connected to said driver and pivoted to said stapler at a first pivot;
   two drive links pivoted together by a drive pin;
   a first one of said links pivoted to said bell crank;
   a second one of said links pivoted to said stapler at a second pivot; and
   a drive cam means mounted on said stapler for motion with respect to said stapler and for engaging and moving said drive pin to operate said driver;
   said drive cam means comprising a partially curved and partially straight cam surface.

2. In a surgical stapler as in claim 1, a four-bar linkage, wherein said cam surface presents a drive surface of varying inclination to said drive pin during movement of said cam.

3. In a surgical stapler as in claim 1, a four-bar linkage wherein said second link forms a second link angle with respect to a first reference line, wherein a line, normal to the tangent point of the cam surface contact with the drive pin, forms a cam angle with respect to a second reference line parallel to said first reference line, and wherein the value of the second link angle, minus the value of the cam angle, equals a complementary angle, which complementary angle varies throughout operation of said linkage.

4. In a surgical stapler as in claim 1, a four-bar linkage operable for driving said staple driver, upon application of an input force thereto, through staple transport and forming stages, said input force changing from about 1.4 pounds to about 0.6 pounds during said transport stage and increasing from about 0.6 pounds to about 4.3 pounds during said forming stage.

5. In a surgical stapler as in claim 3, a four-bar linkage, wherein said linkage produces an increasing mechanical advantage from the beginning to the end of an operating cycle.

6. In a surgical stapler as in claim 3, a four-bar linkage, wherein said linkage requires input forces for operation thereof and wherein the change in said complementary angle substantially leads changes in the required input forces from the end of the transport stage through the forming stage.

7. In a surgical stapler as in claim 3, a four-bar linkage, wherein said staple driver moves through staple transport and staple forming stages, wherein said linkage moves through respective staple transport and forming stages, and wherein said complementary angle decreases during an initial transport stage movement of said linkage and increases during the forming stage movement of said linkage.

8. In a surgical stapler as in claim 7, a four-bar linkage, wherein said complementary angle decreases from about 45° to about 25° during the transport stage and, during the end of the transport stage through the forming stage, increases from about 25° to about 85°.

9. A surgical stapler having a staple driver movable in a transport stage to move a staple from a first position to a form position, and in a forming stage to form a staple, and a drive linkage for moving said staple driver, said drive linkage comprising:

a bell crank pivoted to said stapler at a first pivot and having a first lever arm operably connected to said staple driver, and a second lever arm;

a first drive link;

a second drive link;

a drive pin pivotally connecting said first and second links at first ends thereof, respectively;

said first drive link pivoted at a second end thereof to said second lever arm of said bell crank;

said second drive link pivoted at a second end thereof to said stapler at a second pivot;

a pivotable trigger means pivoted to said stapler at said first pivot for driving said drive linkage;

a drive cam means mounted on said trigger for motion with said trigger and with respect to said stapler, said drive cam operatively engaging said drive pin; and, said drive cam means comprising a cam surface operatively engaging said drive pin and having a partially curved cam surface and a partially straight cam surface extending from said partially curved cam surface, said cam surface presenting a surface of varying inclination to said drive pin during movement of said trigger means.

10. A surgical stapler as in claim 9, wherein said second link forms a second link angle with respect to a first reference line, wherein a line, normal to a tangent point of the cam surface contact with the drive pin, forms a cam angle with respect to a second reference line parallel to said first reference line, and wherein the value of the second link angle, minus the value of the cam angle, equals a complementary angle, which complementary angle varies throughout operation of said linkage, decreasing during an initial transport stage movement of said linkage and increasing during a forming stage movement of said linkage.

11. A surgical stapler as in claim 10, wherein said linkage is movable to operate said staple driver upon application of variable input forces capable of rotating said trigger means about said first pivot and wherein the variation in said complementary angle leads changes in said variable input forces from the end of said transport stage through said forming stage.

12. A surgical stapler as in claim 11, wherein said complementary angle decreases from about 45° to about 25° during the transport stage and, during the end of the transport stage through the forming stage, increases from about 25° to about 85°.

13. A surgical stapler as in claim 12, wherein said linkage is operable, to drive said staple driver through the transport stage upon application of an input force applied to said trigger means and decreasing from about 1.4 pounds to about 0.6 pounds, and to drive said staple driver through said forming stage upon application of an input force applied to said trigger means and increasing from about 0.6 pounds to about 4.3 pounds.

* * * * *

UNITED STATES PATENT AND TRADEMARK OFFICE
CERTIFICATE OF CORRECTION

PATENT NO. : 4,596,350

DATED : June 24, 1986

INVENTOR(S) : George D.K. Smith & John W. Peter

It is certified that error appears in the above-identified patent and that said Letters Patent is hereby corrected as shown below:

Column 3, line 64, "ro tne crawings it wiii" should be --to the drawings it will--

Column 9, line 67, "sprin9" should be --spring--

Column 10, line 47, before "stage" insert --transport--

Column 10, line 47, after "stage" insert --to the beginning of the staple forming stage--

Column 15, line 6, "line" should be --link--

Column 15, line 49, "requires" should be --required--

Signed and Sealed this

Twenty-fifth Day of November, 1986

Attest:

DONALD J. QUIGG

Attesting Officer

Commissioner of Patents and Trademarks